(12) United States Patent
Zerbinati et al.

(10) Patent No.: US 11,324,434 B2
(45) Date of Patent: May 10, 2022

(54) APPARATUS AND PROCESS FOR AN ECG SIGNAL ANALYSIS

(71) Applicant: 365 GIORNI S.R.L., Milan (IT)

(72) Inventors: Umberto Renato Zerbinati, Pavia (IT); Nicola Zerbinati, Pavia (IT)

(73) Assignee: 365 GIORNI S.R.L., Milan (IT)

( * ) Notice: Subject to any disclaimer, the term of this patent is extended or adjusted under 35 U.S.C. 154(b) by 0 days.

(21) Appl. No.: 16/319,003

(22) PCT Filed: Jul. 3, 2017

(86) PCT No.: PCT/IB2017/053999
§ 371 (c)(1),
(2) Date: Jan. 18, 2019

(87) PCT Pub. No.: WO2018/015830
PCT Pub. Date: Jan. 25, 2018

(65) Prior Publication Data
US 2019/0261879 A1    Aug. 29, 2019

Related U.S. Application Data

(60) Provisional application No. 62/364,602, filed on Jul. 20, 2016.

(51) Int. Cl.
*A61B 5/316* (2021.01)
*A61B 5/00* (2006.01)
*A61B 5/318* (2021.01)

(52) U.S. Cl.
CPC .............. *A61B 5/316* (2021.01); *A61B 5/318* (2021.01); *A61B 5/7203* (2013.01); *A61B 5/7282* (2013.01)

(58) Field of Classification Search
CPC . A61B 5/04012; A61B 5/0402; A61B 5/7203; A61B 5/7282
(Continued)

(56) References Cited

U.S. PATENT DOCUMENTS

2004/0230128 A1* 11/2004 Brockway ................ A61N 1/05
                                                                    600/510
2008/0183093 A1*  7/2008 Duann .................. A61B 5/0464
                                                                    600/516
(Continued)

FOREIGN PATENT DOCUMENTS

CN          104027105 A      9/2014

OTHER PUBLICATIONS

International Search Report and Written Opinion, dated Oct. 19, 2017, 14 pages total.

*Primary Examiner* — Amanda K Hulbert
(74) *Attorney, Agent, or Firm* — Vorys, Safer, Seymour & Pease

(57) ABSTRACT

Provided is a process for analysing a dirty ECG tracing, the dirty tracing including a clean ECG tracing, emitted by a main source, and a noise signal emitted by at least one noise source, the method including at least one preliminary phase of breaking down the dirty ECG tracing in a clean ECG tracing and a noise signal by means of an ICA-type analysis, at least one first phase wherein the dirty ECG tracing is discretized for intervals of time in portions of electrical signal, at least one second phase, wherein at least one Gaussian parameter of the portions of electrical signal is evaluated, at least one third phase, wherein one of the portions of electrical signal is selected, in the same interval of time, on the basis of at least one Gaussian parameter and wherein the portion of electrical signal selected is the first portion.

13 Claims, 6 Drawing Sheets

(58) Field of Classification Search
USPC .......................................................... 600/509
See application file for complete search history.

(56) References Cited

U.S. PATENT DOCUMENTS

| 2012/0071730 | A1* | 3/2012 | Romero | A61B 5/046 |
| | | | | 600/301 |
| 2014/0073861 | A1* | 3/2014 | Rodriguez-Llorente | ................... |
| | | | | A61B 5/7246 |
| | | | | 600/301 |
| 2016/0022164 | A1 | 1/2016 | Brockway et al. | |

* cited by examiner

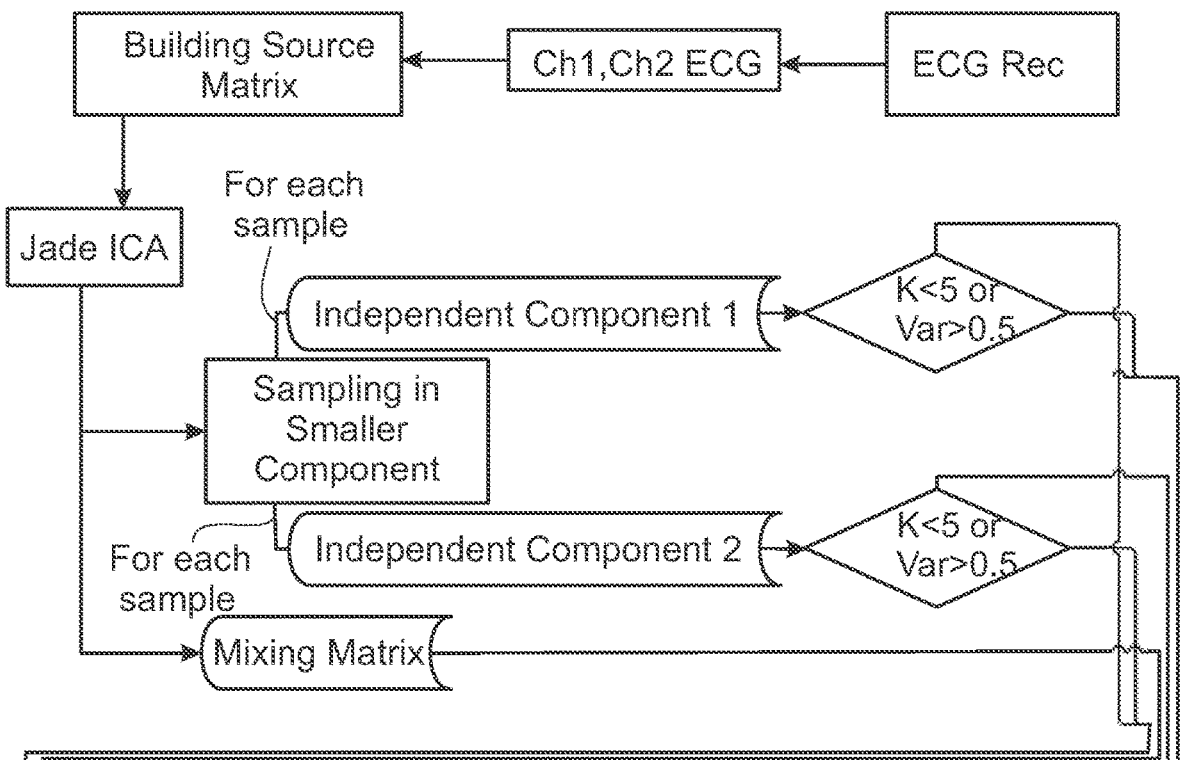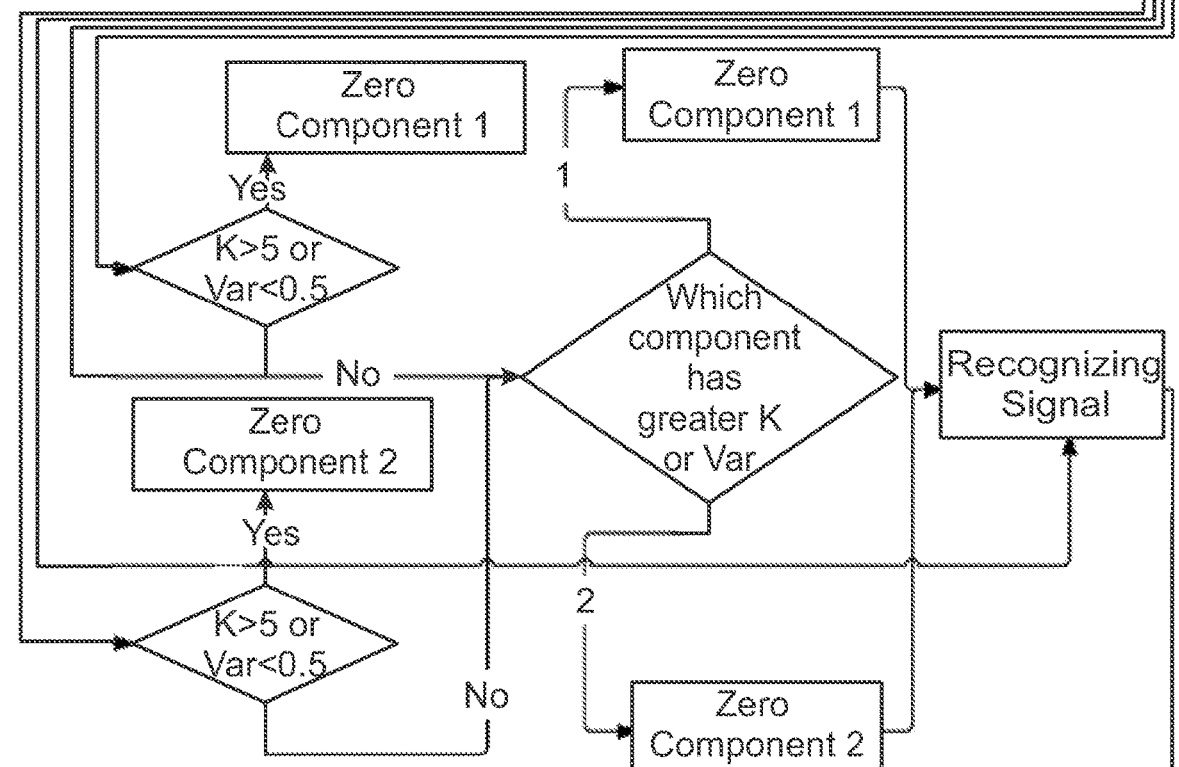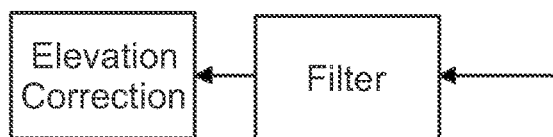
Fig. 1

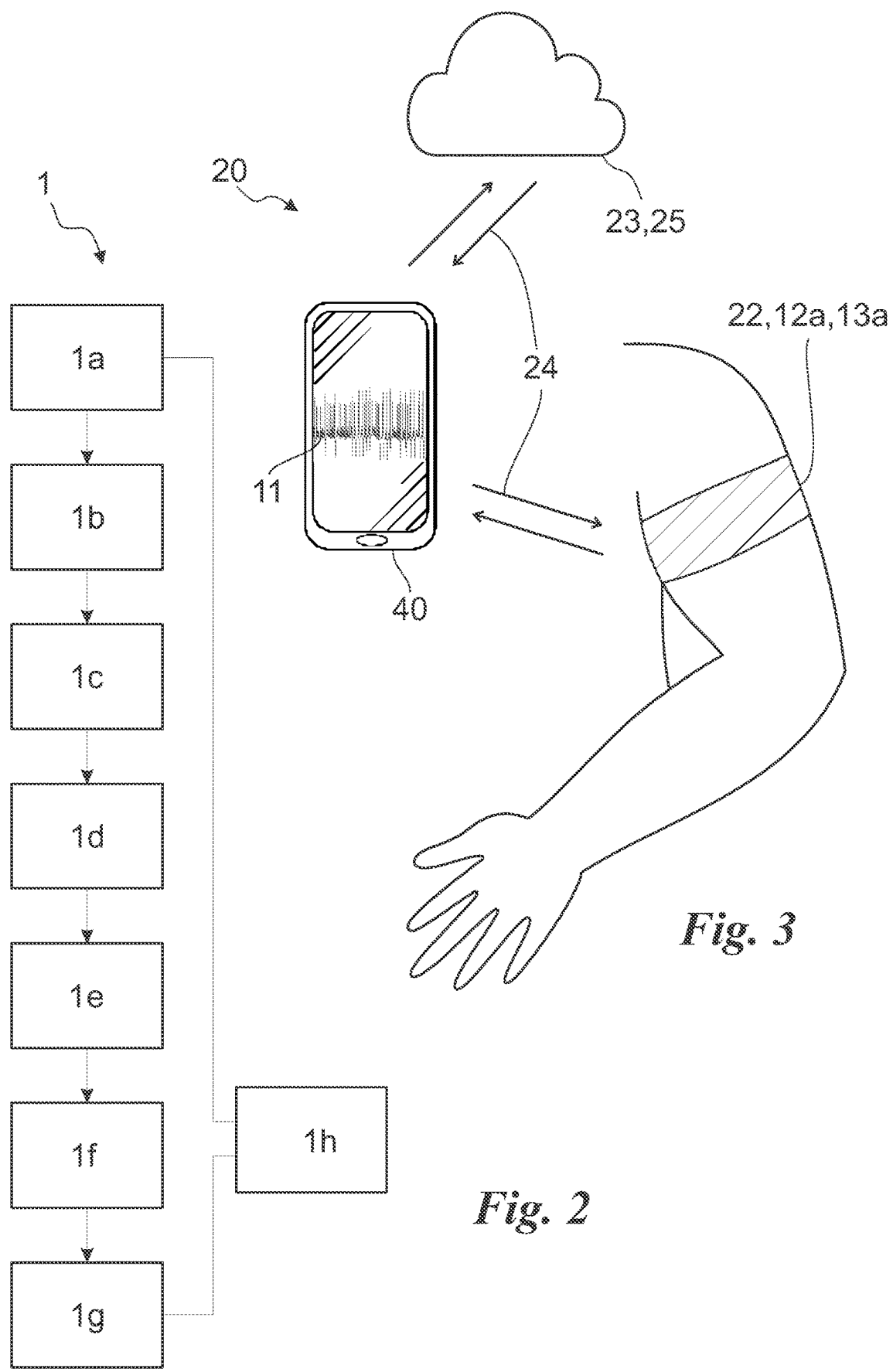

APPARATUS AND PROCESS FOR AN ECG SIGNAL ANALYSIS

The present invention relates to an apparatus and process for an ECG signal analysis of the type specified in the preamble of the first claim.

In particular, the invention relates to an apparatus and the relative operating process that allows ECG signals to be acquired, stored and reprocessed in the presence of noise sources for analysis, for example, in the field of medicine.

At the current state of the art, various methodologies and apparatuses are known by means of which it is possible to acquire electrical signals from the human body for monitoring activities related to various organs in the body, such as, for example, muscular or pulmonary activity or the heartbeat.

Conventionally, these physiological activities are characterised by a mainly periodic, substantially impulsive type trend, which is recorded using electronic instruments suitable for collecting electrical type input signals.

However, the electrical signals are not clean, but inside, they contain components of interest, mixed with other noise or disturbance components depending on the recording carried out.

Included among the various disturbances, which can be found in the input signals is interference caused by the electrical connections used for the acquisition system, noise caused by moving electrodes caused, for example, by patients moving, noise from the acquisition apparatus and other.

Consequently, the acquisition of the signals requires precision and possibly filters that can distinguish the source of interest from unwanted background noises.

Included among the devices and processes, which exist at the moment, are the so-called cardiac Holter devices.

The cardiac Holter monitoring, or the Holter monitoring, is a process characterised by the application of a plurality of electrodes on the chest connected to a portable apparatus (a small battery-operated recorder), which the user wears for a fixed period of time, which is established, for example, by the doctor.

The period of use can be for 24 hours or longer and during this time, the apparatus is suitable for recording a user's electrocardiogram continuously while he/she carries out normal, everyday activities.

Cardiac Holter devices therefore have signal filtering processes, which can be based substantially on two different types of analyses of the variables in question.

These analytical processes are known as PCA and ICA and said processes are generally suitable for reducing the quantity of data measured into a quantity of components that is substantially lower in order to define only those of interest. PCA is understood as an analysis of the signals on the main components, which uses the first and second statistical moments extrapolated from the data measured. In particular, this process is based on the assumption that the data is characterised by marked Gaussianity.

Gaussianity is understood as the tendency of a set of statistical data or random variables to assume a normal distribution. In view of the central limit theorem, this normal distribution is characterised, in a first approximation, by casual variables or real values, which tend to centre around a single mean value.

Therefore, the associated probability density function graph is symmetrical and has a bell shape, which is known as Gauss's bell curve.

Instead, the ICA analysis processes consist of analyses on the independent components, which include statistical moments of a higher nature compared to the PCA analyses, based on the assumption that there is mutual statistical independence of the source of the signals understood as non-Gaussian. These represent a particular case of the blind source separation theory.

The statistical process finds the independent components, latent variables or sources, maximising the statistical independence of the estimated components. Non-Gaussianity represents an index for measuring the independence of the components and can be measured, for example, by kurtosis or approximations of negentropy. Mutual information is another common criterion for measuring statistical independence of signals.

The described known art comprises a number of important inconveniences.

In particular, cardiac Holter devices foresee the application of a plurality of electrodes on the human body, which are uncomfortable to wear and located on various parts of the chest or the body in general.

In fact, they are mostly positioned according to a known mapping based, for example, on the electrocardiographic derivations constituting Einthoven's triangle or other.

Furthermore, said electrodes, which conventionally come into contact, do not allow the user wearing them to move freely because when they are moved they generate noise caused by the movement of the contacts and the user.

Therefore, if the user makes a sudden movement, the distortion of the source signal is even greater. Besides the positioning and the quality of the electrodes, there are other factors, which influence the quality of the signal, such as muscle tremors, frequency of sampling and the resolution of the digitalized signal.

In addition, ECG Holter devices comprise a power supply battery for the electrodes that users generally wear on a strap, which represents a further hindrance and obstacle for carrying out normal, everyday activities.

Another important disadvantage of the known art is that the source signal filtering processes used conventionally in ECG Holter devices are inadequate or partially inadequate for extrapolating clean data for heartbeats.

The PCA processes, for example, are based on the assumption that the variables in question are characterised by marked Gaussianity, however, this approximation is only valid for elements, such as noise, but approximate the variables of interest inadequately, especially because of the fact that periodic signals or signals with strong periodicity are typically non-Gaussian.

Instead, as regards the ICA processes, another important disadvantage within the context of the known art is represented substantially by various specific technical problems, in other words the problem of the commutability of the components, the formation of blind spots in the output signal and misalignment of the components.

The commutability of the components is caused by the fact that the conventional ICA processes are not able to extract the exact number of signal sources or the order of arrival of the source signals, which translates into substantial unrecognizability of the noise signal in relation to that of the electrical cardiac activity in some cases.

Whereas, the formation of blind spots can, for example, be attributed to the fact that most ICA systems have pre-set threshold values for signal filtering, which can sometimes lead to all of the information being eliminated, consequently generating gaps in the information.

Finally, the misalignment of the components is caused by the fact that the conventional ICA techniques are not even able to provide the scalar value of the sources (as well as the signal) and consequently, in some cases, especially in the presence of a particularly noisy signal, the extrapolated data can be misaligned in sections.

In this situation, the technical task at the root of the present invention is to develop an apparatus and process for analysing an ECG tracing capable of substantially overcoming at least part of the stated inconveniences.

Within the scope of said technical task, an important object of the invention is to obtain an apparatus that is both easy to wear and doesn't cause a hindrance to users or time limits related to its use as a result of the nature of the system.

Another important object of the invention is to develop an apparatus and process for analysing an ECG tracing that can reproduce the signal, for example, of a heartbeat with an opportune representation cleared of the noisy components deriving from sources of disturbance.

Another important technical task of the invention is to define an apparatus and process for analysing an ECG tracing, which is not affected by the problems encountered in the prior art and which is, consequently, able to distinguish the signal emission sources and generate filtered output without blind spots or unwanted misalignments.

The technical task and specified aims are achieved by an apparatus and process for analysing an ECG tracing as claimed in the attached claim 1. Preferred embodiments are described in the dependent claims.

The characteristics and advantages of the invention are clarified below by a detailed description of preferred embodiments of the invention, with reference to the accompanying drawings, wherein:

FIG. 1 shows an operational diagram of the device according to the invention;

FIG. 2 illustrates a diagram of the process for analysing an ECG tracing;

FIG. 3 is a diagram of the apparatus for analysing an ECG tracing;

Figure 4:
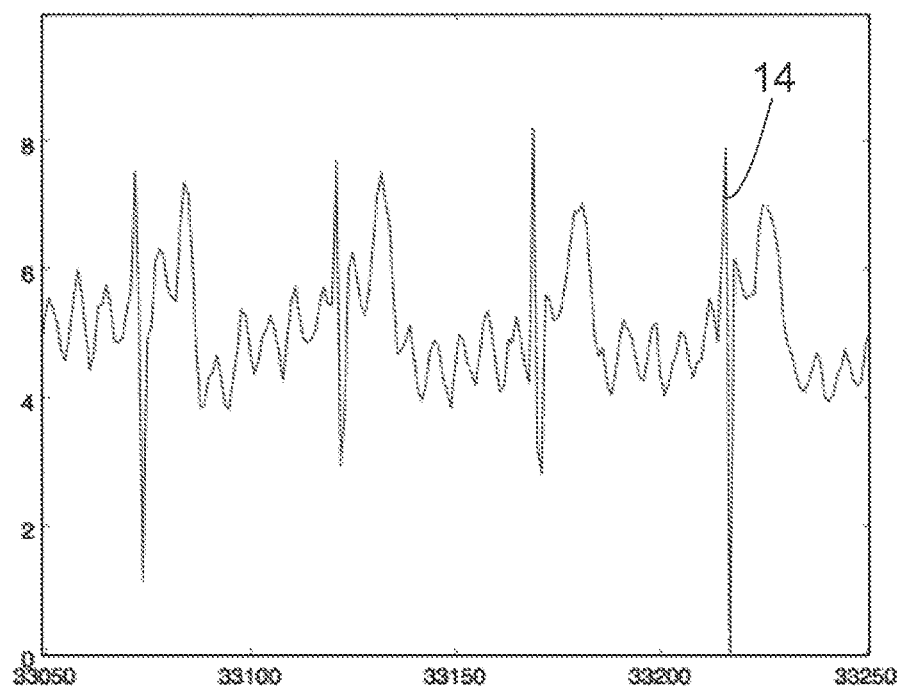
FIG. 4 represents a dirty ECG tracing.
Figure 5A:
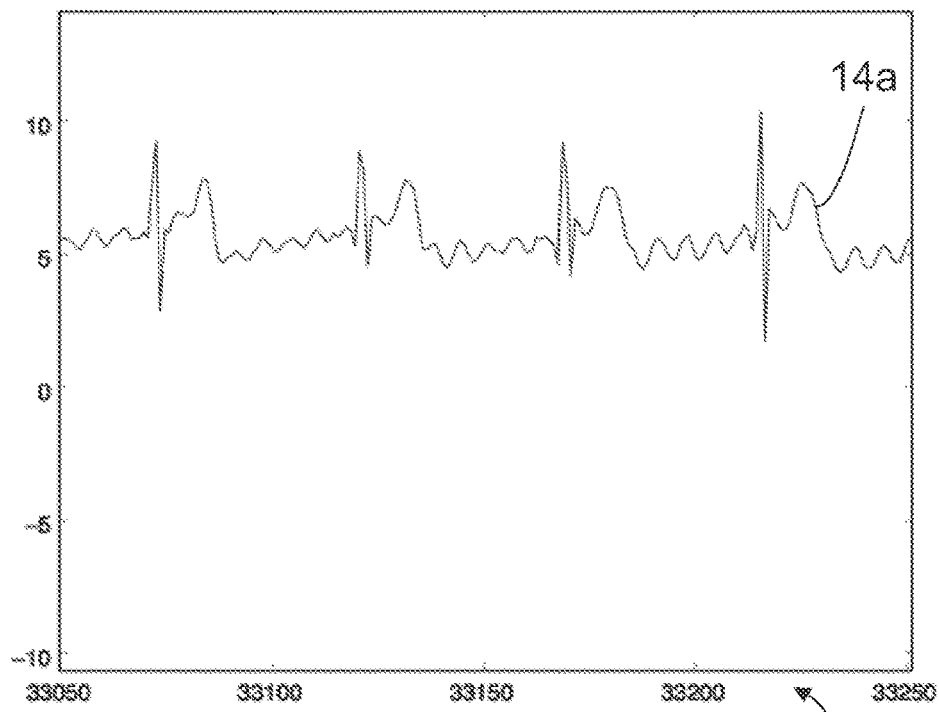
FIG. 5a shows a clean ECG tracing.
Figure 5B:
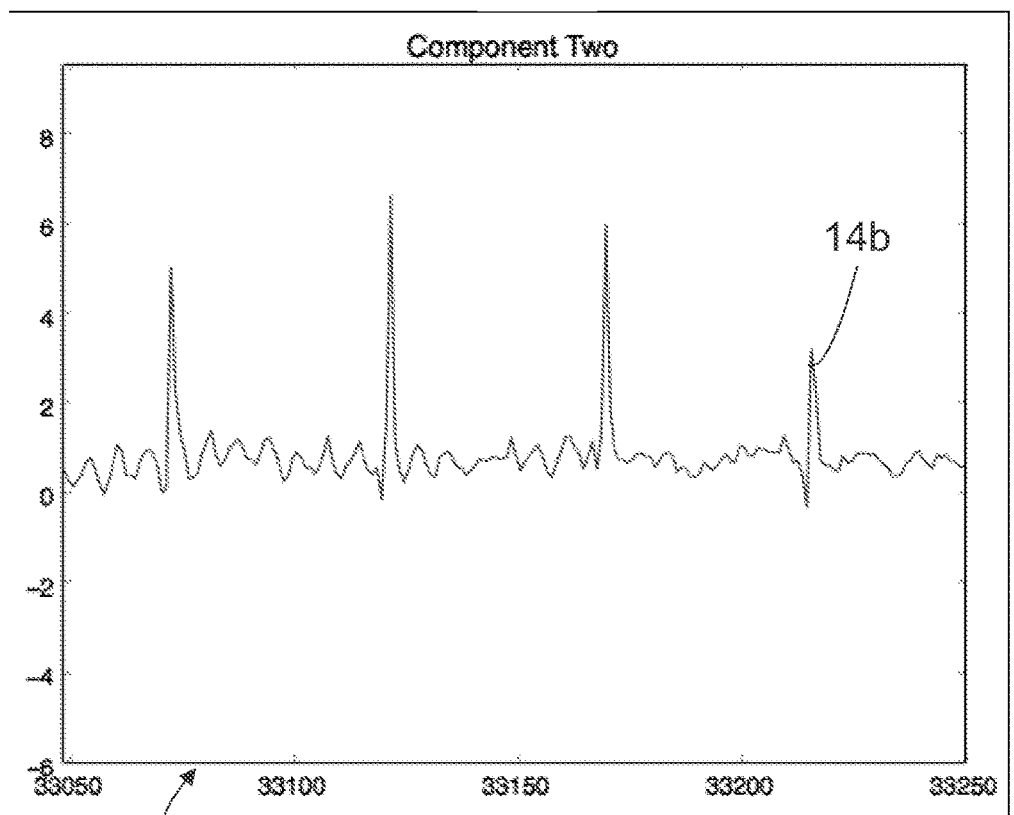
FIG. 5b illustrates a noise signal.
Figure 6:
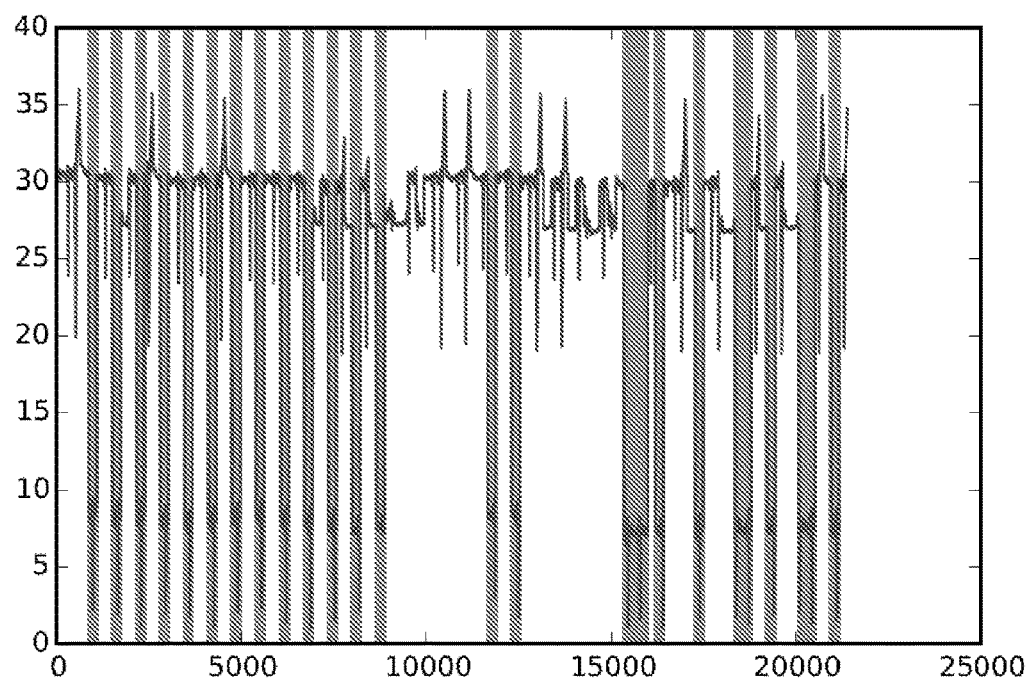
FIG. 6 represents the discretization intervals on a clean ECG tracing.
Figure 7:
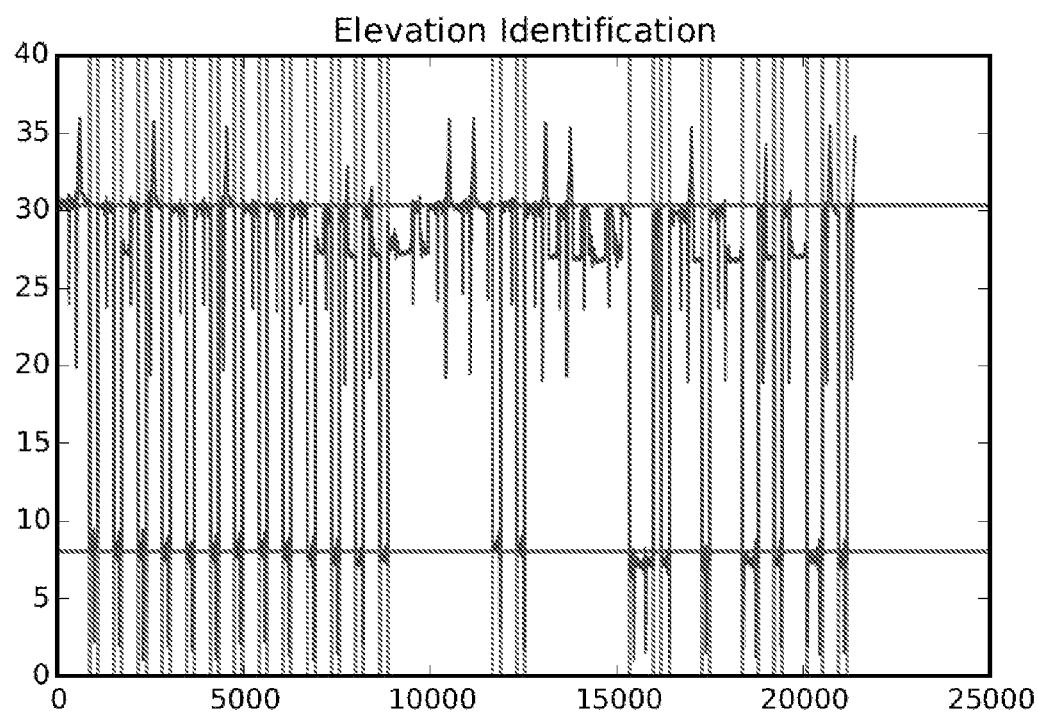
FIG. 7 shows the equipotential lines of a clean misaligned ECG tracing.
Figure 8:
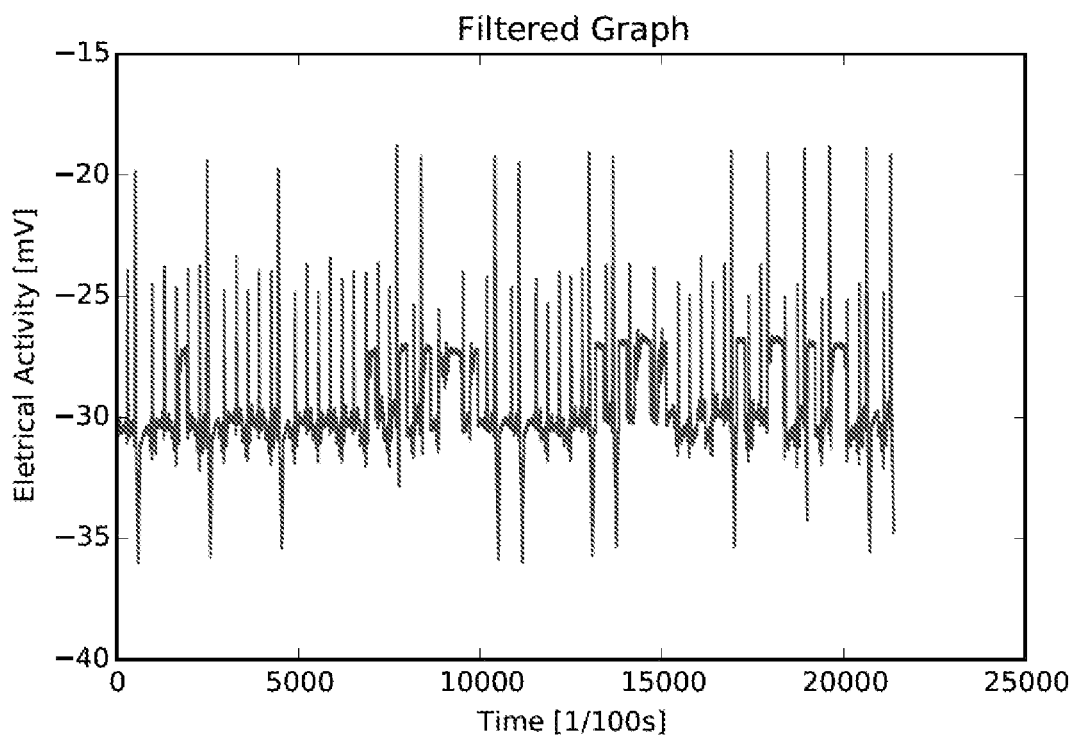
FIG. 8 illustrates a clean aligned ECG tracing.
Figure 9A:
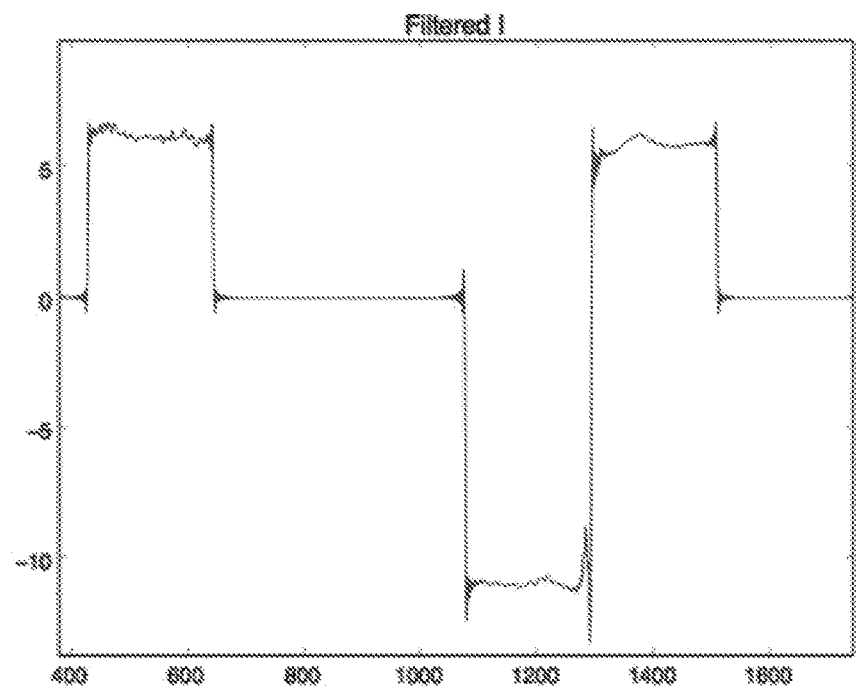
FIG. 9a is an example of an ECG tracing comprising blind spots.
Figure 9B:
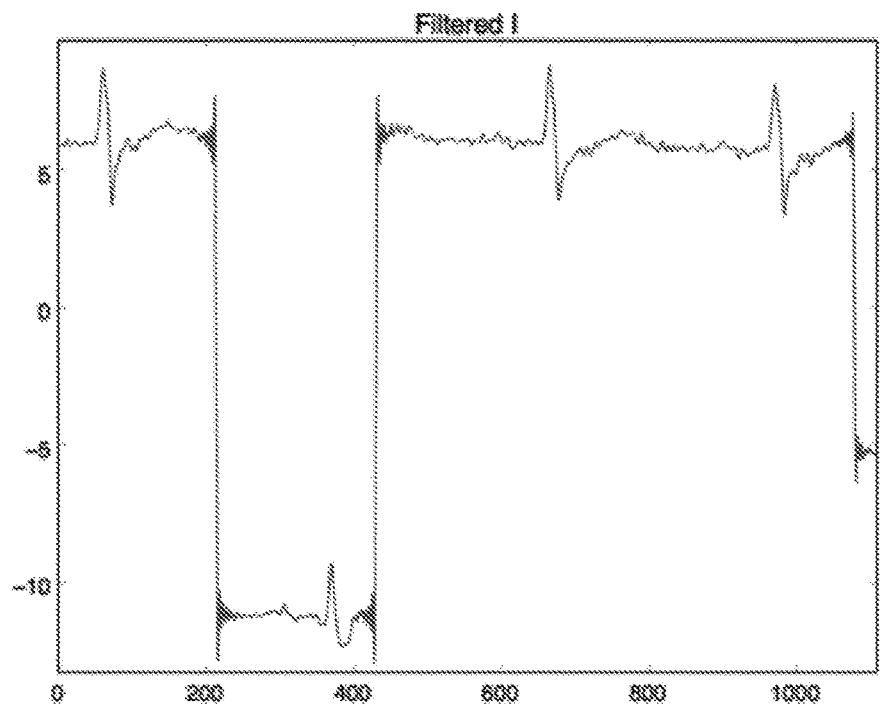
FIG. 9b is an example of an ECG tracing comprising misalignment.

In this document, when measurements, values, shapes and geometrical references (such as perpendicularity and parallelism) are associated with words, such as "approximately" or other similar terms, for example "practically" or "substantially", they shall be understood as except errors of measurement or inaccuracies resulting from production and/or manufacturing errors and, above all, except a slight divergence from the value, measurement, shape or geometrical reference with which it is associated. For example, if said terms are associated with a value, they preferably indicate a divergence of no more than 10% of the same value.

Furthermore, when terms such as "first", "second", "greater", "lower", "principal" and "secondary" are used, they do not necessarily identify an order, a relationship priority or relative position, but they may simply be used to distinguish different components more clearly.

With reference to the Figures, the process for analysing a dirty ECG tracing G according to the invention is globally indicated with number 1.

With reference to the Figures, the apparatus for analysing a dirty ECG tracing according to the invention is globally indicated with number 20.

The apparatus 20 for analysing a dirty ECG tracing comprises at least one sensor device 22, memorisation means 23, connection means 24 and at least one data processing device 25.

The sensor device 22 preferably consists of an electrode, for example, of the type known and commonly used for acquiring cardiac signals.

It also comprises, for example, a suction cup comprising a portion in polymeric material around a central metal core suitable for acquiring electrical type signals.

The sensor device 22 can also comprise one or more PADs comprising electro-co-adhesive electrodes suitable for attaching to the user's body.

In any case, the sensor device 22 is preferably suitable for acquiring a dirty ECG tracing 11 emitted, for example, from the user's body.

The dirty ECG tracing 11 can comprise muscular, pulmonary or cardiac signals and generally includes all signals, including mixed ones, which can be emitted by the human body.

The user can be a patient undergoing medical treatment, but he/she may also be a sportsman or simply a person intending to monitor his/her bodily functions.

The apparatus 20 preferably also comprises only one sensor device 22, for example, attached to the human body and, more specifically to a limb, by means of elastic bands of a known type or Velcro laces.

However, the apparatus 20 can also comprise a plurality of devices 22, for example, conventionally attached to the human body.

By conventionally, we mean the classical structure of cardiac Holter devices, which involve the use of twelve devices 22 arranged along the three bipolar derivations of the limbs, the three unipolar derivations of the limbs and the six precordial derivations.

In any case, as stated, the recorded signals are preferably a dirty ECG tracing 11 comprising one or more signals.

In particular, the dirty ECG tracing 11 preferably consists of mixed signals comprising, for example, a plurality of signals and, consequently, these comprise at least one clean ECG tracing 12, emitted from a main source 12a and a noise signal 13 emitted from at least one noise source 13a.

The clean ECG tracing 12 preferably substantially corresponds to a conventional cardiac type signal, in other words, wherein the wave sections P, Q, R, S, T, U as defined by Einthoven are highlighted.

Said signal is characterised, for example, by periodicity or better said, predominantly homogenous frequency, which determines its distinctly non-Gaussian behaviour. In fact, the Gaussianity of a signal, as said previously, substantially lies in the fact that random independent events, such as, for example, signal noises or disturbances, tend to assume a normal type of distribution or Gauss distribution, which consists of a trend tending towards an average value.

The main source 12a coincides, for example, with the user's heart.

However, the main source 12a must preferably be considered as the heartbeat perceived by the sensor device 22 and therefore, it must preferably be considered level with said sensor device 22, in other words like the cardiac electrical activity level with the sensor device 22.

Instead, the noise signal 13 is, for example, a disturbance signal of the clean ECG tracing and can correspond, for example, to the noise emitted by muscular activity or also the noise emitted by lung activity or other.

The noise source 13a is, for example, consequently, a different organ to the heart, or other types of disturbances caused by acquisition from the sensor device 22.

As with the main source 12a, the noise source preferably coincides with the disturbance signal perceived by the sensor device 22 and therefore, it must preferably be considered level with the sensor device 22.

The sensor device 22, which is preferably an elastic band, can also comprise movement sensors.

These movement sensors can be, for example, accelerometric type sensors, or gyroscopic sensors or other.

Sensors can be present, for example, for detecting indirect movement, such as common humidity sensors for the sweat of a user wearing the sensor device 22 or said sensors can be suitable for measuring the energy consumed by the user.

Since the movement sensors may be located on the sensor device 22, they are suitable for recording the movement of the sensor device 22 and consequently also for recording the movement of the main source 12a and the noise source 13a.

The memorisation means 23 can be physical supports, such as, for example, common memory cards, or they can be virtual supports of a known type.

The memorisation means 23 preferably comprise a cloud-type memory support and they can comprise the data processing device 25 suitable for cleaning the dirty ECG tracing 11 in a clean ECG tracing 12.

Whereas, the connection means 24 are preferably suitable for connecting the sensor device 22 and the memorization means 23. Said connection means can be common electrical connection wires, for example, or they can preferably be wireless type means, such as infrareds, Bluetooth® or other.

Furthermore, the connection means 24 can preferably include one or more auxiliary data processing devices 40 between the memorisation means 23 and the sensor device 22.

The auxiliary data processing device 40 can be, for example, any electronic means fitted with a processor and a screen. For example, the auxiliary data processing device 40 can be a tablet, a computer or other.

The auxiliary data processing device 40 is preferably a smartphone.

In particular, it is preferably suitable for allowing the user to display the acquired dirty ECG tracing 11 in real time, for example by means of a specific application.

In addition, the auxiliary data processing device 40 is also suitable for allowing the clean ECG tracing to be displayed by means of the data processing device 25 and recorded on the memorisation means 23.

The data processing device 25 is a common type of electronic processor, such as, for example, a processor or other, comprising software suitable for performing a plurality of commands.

The data device 25 is preferably included or coincides with the memorisation means 23, however, it may also be included or coincide with the auxiliary data processing device 40.

The data processing device 25 is preferably suitable for performing process 1.

The process 1 for analysing a dirty ECG tracing 11 comprises at least one preliminary phase 1a, a first phase 1b, a second phase 1c, a third phase 1d, a fourth phase 1e, a fifth phase 1f, a sixth phase 1g and a seventh phase 1h.

The preliminary phase 1a consists of breaking down the dirty ECG tracing 11 into the clean ECG tracing 12 and noise signal 13 by means of an ICA-type analysis (analysis of the independent variables).

ICA-type analyses consist of computational processing methods, which serve to separate a multivariate signal into its additive sub-components, assuming that there is a mutual statistical independence of the source of the non-Gaussian signals and this is a particular case of the "blind source separation".

Among the various types of ICA analyses documented in literature (FastICA, infomax and other), a JADE-type algorithm (Joint approximation diagonalization of Eigen's matrix), which is subsequently explained in further detail, is preferably used in the preliminary phase 1a.

The first phase 1b preferably consists of a discretization of the dirty ECG tracing 11 for time intervals. This discretization consequently leads to a subdivision, depending on the type of discretization chosen, of the dirty ECG tracing 11 into portions of electrical signal 14.

This subdivision is preferably carried out in the time domain and consists of defining $\Delta t$ time intervals with values, for example, equal to $1 \times 10^{-2}$ s.

Furthermore, the portions of electrical signal 14 comprise, in turn, a first portion 14a and a second portion 14b.

The first portion 14a preferably comprises part of the tracing for the clean ECG 12, while the second portion 14b comprises part of the noise signal 13.

The second phase 1c preferably consists of evaluating at least one parameter of Gaussianity or, better said, non-Gaussianity of the portions of electrical signal 14.

Present among the parameters of known Gaussianity for example is kurtosis (or kurtosis moment), variance and negentropy.

The parameters considered are preferably kurtosis and variance.

In this regard, the nth portion of signal 14 is considered as:

$$x(n)=k*s(n)+w(n).$$

Where k is a signal coefficient, s(n) is the nth first portion 14a and w(n) is the nth second signal portion 14b.

Consequently, s(n) preferably represents a typically non-Gaussian type portion of signal 14, while w(n) represents a typically Gaussian-type portion of signal 14.

The moment defined by the cumulant or semi-invariant of the fourth order is defined as kurtosis and can be calculated as:

$$\tilde{K}(x)=E(x^4)-3[E(x^2)]^2$$

where E is the function defining the expected value.

The term kurtosis represents the Gaussianity of the signal and tends to the zero value when the signal x(n) is substantially Gaussian.

As x(n) is subdivided into a first portion 14a or s(n) and a second portion 14b or w(n), the Gaussianity of the portion of signal 14 x(n) only emerges if the second portion 14b is present.

Therefore, an indicator of the presence of the noise or second portion 14b is the kurtosis value, which is close to the zero value for signals with disturbances.

As for the variance, it is defined by:

$$\sigma^2 = \frac{\sum_{i=1}^{n}(x_i - \mu)^2}{n}$$

Where µ is the arithmetic average of the nths $x_n$, in other words $$\mu = \frac{\sum_{i=1}^{n} x_i}{n}.$$

To evaluate Gaussianity with variance, it is preferable to evaluate the disparity between the variance of a distribution of Gaussian noise and the actual distribution of the nth portions of electrical signal 14.

The third phase 1*d* preferably consists of selecting one of the portions of electrical signal 14 in the same time interval (Δt), based on at least one Gaussian parameter. Typically, and preferably the portion of electrical signal, which is selected, is the one defined by lower Gaussianity, in other words the first portion 14*a*.

Specifically, for example, to determine the noise or second portion 14*b*, we must consider the expression corresponding to:

$$|\tilde{K}| < 5 \wedge \sigma^2 > 0.5$$

However, it is possible, in some cases, that this restriction is not sufficient for determining and selecting the first portion 14*a*.

In these cases, for example, both components appear within the interval defined by the previous expression.

Preferably, in this case, a new selection is made.

This selection is preferably made evaluating the portion of electrical signal 14 affected by a higher kurtosis moment, in other words by lower Gaussianity.

This principle, which preferably consists of a substantial rule of non-double cancellation of the components, can be expressed as follows:

$$[\tilde{K}(x_{1,i}) < 5 \wedge \sigma^2(x_{1,i}) > 0, 5] \wedge [\tilde{K}(x_{2,i}) < 5 \wedge \sigma^2(x_{2,i}) > 0, 5] \xrightarrow{yields}$$

if $K(x_{1,i}) < K(x_{2,i})$ then $x_{1,i} = 0$ if $K(x_{1,i}) > K(x_{2,i})$ then $x_{2,i} = 0$ The fourth phase 1*e* consists of recording the first portions of signal 14*a* selected in the third phase 1*d* on a memorisation support. In particular, the memorisation support preferably coincides with the memorisation means 23.

The fifth phase 1*f* consists of the reconstruction of the clean ECG tracing 12 based on the first portions of signal 14*a* recorded in the fourth phase 1*d*.

The clean ECG tracing 12 is consequently preferably all of the portions of signal 14 cleared of the second portions 14*b* and therefore of the noise.

The clean ECG tracing 12 can have a substantially constant trend consequently defining a prevalent equipotential line along which the ECG tracing 12 is distributed.

However, it is possible that the clean ECG tracing 12 is only continuous in sections (see FIG. 2). In this case, the clean ECG tracing 12 defines, for example, a plurality of equipotential lines level with the sections of substantial continuity of the signal. These equipotential lines consequently appear substantially, in this case, misaligned.

Therefore, process 1 comprises the sixth phase 1*g* wherein said prevalent equipotential lines are aligned.

In order to be able to align the equipotential lines, the data processing device 25 analyses and discretizes the portions of electrical signal 14 again preferably with intervals corresponding to Δ=a−b, where the terms a, b are successive time values substantially coinciding and preferably on transition between one equipotential line and another.

In order to be able to evaluate whether there is an elevation or misalignment of the equipotential lines, the integral misalignment rule is used:

$$\frac{\int_a^b f(x)dx}{\int_0^\Delta f(x)dx} * 100 > C$$

Where a and b are the extremes of the interval of discretization, the function $f(x)$ consists of the representative function of the clean ECG tracing 12 and "C" is an arbitrary constant or parameter that can be manipulated.

C is preferably an arbitrary constant or parameter, which depends on the distribution of the input signal, in other words the clean ECG tracing 12, following the integral misalignment rule stated previously.

Specifically, C for example, can take on values comprised between 150 and 200 and more opportunely 175.

Once the misalignments have been identified, it is consequently preferably possible to define a clean ECG tracing 12 substantially aligned with only one prevalent equipotential line.

Finally, in the seventh phase 1*h*, the movement of said main source 12*a* is preferably recorded, as well as said noise source 13*a*. This movement can be recorded during the activity of the data processing device 25 preferably by means of a movement sensor comprised within the sensor device 22.

In particular, the movement of the main source 12*a* and of the noise source 13*a* coincides, for example, with the movement of the sensor device 22.

Each of the phases 1*a*, 1*b*, 1*c*, 1*d*, 1*e*, 1*f*, 1*g*, 1*h* can be undertaken with different times and in a different order to those previously described, provided that the data processing functionality is maintained.

The operation of the apparatus 20 described previously in structural terms is as follows.

The user can position the sensor device 22 in contact with a portion of a limb, for example, using elastic bands, and set the apparatus 20 in operation.

Once the system has been activated, the user can command, for example, the acquisition using the auxiliary data processing device 40.

The sensor device 22 continues to record the dirty ECG tracing 11 and sends the information recorded to the auxiliary data processing device to be displayed and/or to the memorisation means 23 to be recorded.

Once the data has been recorded, the data processing device 25 is activated and analyses the data received again, distinguishing the clean ECG tracing 12 component from that of the noise signal 13.

At this point, the noise signal 13 is eliminated from the recorded information and the next phase consists of aligning the clean ECG tracing 12.

The processed information is consequently saved again on the memorisation means 23 and made available for subsequent visualisation.

In particular, the final recorded data comprising the clean aligned ECG tracing 12 is in vector format and can consequently be accessed by means of any device suitable for displaying said formats.

The operation of this apparatus 20 has no limits in terms of time, other than those defined by the supply, the variable, the auxiliary data processing device 40 or by the special memory inside the memorization means 23.

Consequently, it is possible to access, for example, a time history of an extensive ECG tracing and, thanks to the movement sensors, evaluate whether any physical activity has been carried out in some sections.

The apparatus and process for analysing a dirty ECG tracing 1 according to the invention presents important advantages.

In fact, the apparatus 20 for a dirty ECG tracing 1 is composed of a plurality of elements, which allow the user to monitor and observe data referring to cardiac behaviour without any particular impediment or hindrance.

Furthermore, as it is not necessary to use a plurality of devices 2 thanks to the precision and filtering permitted by process 1 according to the invention, the apparatus 20 does not require a large battery to supply the devices 2 as is the case with traditional cardiac Holter devices.

Another advantage of the apparatus and process for a dirty ECG analysis is that the analysis traditionally known as ICA is boosted, and consequently provides consultable data, which is more representative and realistic.

Specifically, two previously described basic problems relating to said technique are overcome.

In fact, the calculation algorithms not only allow the signals acquired by the sensor device 22 going into the memorization means 23, to be distinguished blindly, a solution, which already exists at the current state of the art, but also the clean ECG signal 12 to be distinguished carefully from the noise signal 13, based on specific Gaussian parameters.

Thus, in this sense, the problem of component permutation found in traditional ICA analysis systems is overcome.

A further advantage also comes from the problem solving of "blind spots" and output signal misalignments.

The algorithms used make it possible to avoid the elimination of all of the data for fractions of signal that do not exceed the fixed margin thresholds.

For this reason, the clean ECG signal 12 does not contain missing portions of data.

Furthermore, process 1 also makes it possible to solve the problem of misalignment of the prevalent equipotential lines of the clean ECG signal 12 as it allows the misaligned portions to be detected and aligned with a line of reference by means of integration analysis.

The invention is subject to variations falling within the scope of the inventive concept defined by the claims.

In this context, all of the parts can be replaced with equivalent elements, using any materials, shapes and sizes.

The invention claimed is:

1. A process for analysing a dirty electrocardiogram (ECG) tracing said dirty ECG tracing comprising a clean ECG tracing, emitted by a main source, and a noise signal, emitted by at least one noise source, said process comprising:
    at least one preliminary phase of breaking down said dirty ECG tracing into said clean ECG tracing and a noise signal by means of an Independent Component Analysis-type (ICA-type) analysis,
    at least one first phase wherein said dirty ECG tracing is discretized for intervals of time in portions of electrical signal,
    wherein said portions of electrical signals comprising a first component, part of said clean ECG tracing, and a second component, part of said noise signal,
    at least one second phase wherein at least one Gaussianity parameter of said portions of electrical signal is evaluated,
    at least one third phase wherein one of said components of electrical signal is selected, comparing the respective Gaussianity of said components in said same interval of time, basing on said at least one Gaussianity parameter, so that at least one of said component is selected among said portions of electric signal and
    said single selected portion of electrical signal corresponding always to said first component; and
    a further phase wherein the movement of said main source is recorded by an accelerometer, as well as said noise source, said movement recorded making it possible to identify whether the dirty ECG tracing was obtained under stress;
    wherein the ECG tracing comprises signals acquired from a portable monitoring device which a user wears for a fixed period of time, the portable monitoring device configured to perform cardiac Holter monitoring by application of a plurality of electrodes as sensor devices on a chest of a user and a limb of the user, said sensor devices connected to a portable apparatus comprising a battery operated recorder, wherein at least the sensor device on the limb of the user comprises the accelerometer.

2. The process for analysing a dirty ECG tracing according to claim 1, wherein said at least one Gaussianity parameter is at least one chosen from kurtosis, variance and negentropy.

3. The process for analysing a dirty ECG tracing according to claim 1, wherein the component of said portion of electrical signal made up of a higher kurtosis moment is selected in said at least one third phase.

4. The process for analysing a dirty ECG tracing according to claim 1, comprising a fourth phase wherein said first components of signal selected in said third phase are recorded on a memorisation support.

5. The process for analysing a dirty ECG tracing according to claim 4, comprising a fifth phase wherein said clean ECG tracing is reconstructed on the basis of said first components of signal recorded in said fourth phase, said clean ECG tracing defining at least one prevalent equipotential line.

6. The process for analysing a dirty ECG tracing according to claim 5, wherein said clean ECG tracing defines a plurality of prevalent equipotential lines in said fifth phase and said method comprises a sixth phase wherein said prevalent equipotential lines are aligned.

7. An apparatus for analysing a dirty ECG tracing, comprising:
    at least one sensor device configured for acquiring said dirty ECG tracing,
    memorisation means configured for enabling the recording of information,
    connection means configured for connecting said sensor device and said memorisation means, and
    at least one data processing device comprising means for carrying out said process in claim 1;

wherein the at least one sensor device comprises a movement sensor wherein the movement sensor is an accelerometer, wherein the at least one sensor device is configured to be part of a portable monitoring device for a user to wear for a fixed period of time, the portable monitoring device configured to perform cardiac Holter monitoring comprising a plurality of electrodes as sensor devices for application on a chest of a user and a limb of the user, said sensor devices connected to a portable apparatus comprising a battery operated recorder, wherein at least one of the sensor devices for application on the limb of the user comprises the accelerometer.

8. The apparatus for analysing a dirty ECG tracing according to claim 7, wherein said sensor device is made up of an element chosen from an elastic band comprising an electrode and the movement sensor for said sensor device and at least a PAD comprising an electro-co-adhesive electrode suitable for attaching to the body of the user.

9. The apparatus for analysing a dirty ECG tracing according to claim 8, wherein said connection means are of a wireless type and comprise an auxiliary data processing device configured for communicating with said sensor device and said memorisation means, said data processing device being a cloud-type remote server, also including said memorisation means, said auxiliary data processing device configured for allowing the display of said dirty ECG tracing in real time and/or said clean ECG tracing processed by said data processing device and recorded in said memorisation means.

10. The apparatus for analysing a dirty ECG tracing according to claim 7, wherein said connection means are of a wireless type and comprise an auxiliary data processing device configured for communicating with said sensor device and said memorisation means, said data processing device being a cloud-type remote server, also including said memorisation means, aid auxiliary data processing device configured for allowing the display of said dirty ECG tracing in real time and/or said clean ECG tracing processed by said data processing device and recorded in said memorisation means.

11. The process for analysing a dirty ECG tracing according to claim 2, comprising a fourth phase wherein said first components of signal selected in said third phase are recorded on a memorisation support.

12. The process for analysing a dirty ECG tracing according to claim 11, comprising a fifth phase wherein said clean ECG tracing is reconstructed on the basis of said first components of signal recorded in said fourth phase, said clean ECG tracing defining at least one prevalent equipotential line.

13. The apparatus for analysing a dirty ECG tracing according to claim 7, wherein the at least one sensor device is part of the portable monitoring device for a user to wear for a fixed period of time, the portable monitoring device configured to perform cardiac Holter monitoring comprising the plurality of electrodes as sensor devices for application on a chest of a user and a limb of the user, said sensor devices connected to the portable apparatus comprising the battery operated recorder, wherein the memorization means comprises the battery operated recorder, wherein at least one of the sensor devices for application on the limb of the user comprises the accelerometer.

* * * * *